United States Patent [19]

Johansson et al.

[11] 4,041,962
[45] Aug. 16, 1977

[54] IMPLEMENT TO FACILITATE REMOVING BACTERIAL COATING FROM THE INTERSTITIAL AREAS OF ADJACENT TEETH AND CLEANING THE CREVICES THEREBETWEEN

[76] Inventors: Erik Gunnar Johansson, Sagverksgatan 40, 122 41 Enskede; Bengt Ture Hubertus Blomberg, Artillerigatan 48 nb, 114 45 Stockholm; Bernt Holger Elmquist, Fribovagen 2 E, 151 44 Sodertalje, all of Sweden

[21] Appl. No.: 553,419

[22] Filed: Feb. 26, 1975

[30] Foreign Application Priority Data

Feb. 27, 1974 Sweden ................................ 7402562
Feb. 27, 1974 Sweden ................................ 7402563

[51] Int. Cl.² ........................................... A61C 15/00
[52] U.S. Cl. ............................................... 132/91
[58] Field of Search ........................ 132/89, 90, 91, 92

[56] References Cited

U.S. PATENT DOCUMENTS

| 1,414,604 | 5/1922 | Thum | 132/91 |
| 1,996,205 | 4/1935 | Jackson | 132/89 |
| 2,444,638 | 7/1948 | Dobbins | 132/92 R |
| 2,517,806 | 8/1950 | Streiler | 132/91 |
| 2,981,264 | 4/1961 | DeFelice | 132/91 |
| 3,050,072 | 8/1962 | Diener | 132/93 |
| 3,078,856 | 2/1963 | Bender et al. | 132/93 |
| 3,474,799 | 10/1969 | Cappello | 132/91 |
| 3,759,273 | 9/1973 | Kraus | 132/92 R |

FOREIGN PATENT DOCUMENTS

| 8,803 | 4/1908 | United Kingdom | 132/89 |

Primary Examiner—G.E. McNeill
Attorney, Agent, or Firm—Blanchard, Flynn, Thiel, Boutell & Tanis

[57] ABSTRACT

An implement for removal of bacterial coating from the interstitial areas of adjacent teeth and for cleaning the crevices between such teeth comprises a handle arranged to be securely held by the hand of the user. A toothpick or the like is preferably tapered and of triangular cross section and is frictionally held at substantially right angles to the plane of the handle in a bushing mounted in a hole through one end of the handle so as to permit the rotation of the toothpick and thereby facilitate its entry between adjacent teeth for cleaning. A bent-up portion of the handle at its opposite end facilitates firm holding and guiding of the implement. Conveniently the bent-up portion is fork-shaped and cooperates with a fastening device on the adjacent portion of the handle for supporting a dental floss tensioned between the ends of the tines of the fork for interdental cleaning supplementary to the use of the toothpick.

7 Claims, 6 Drawing Figures

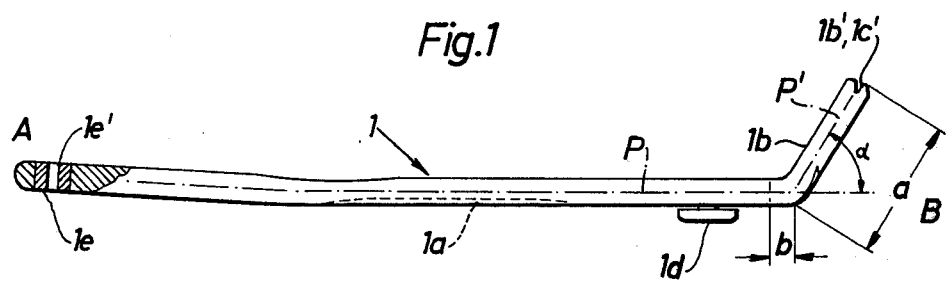
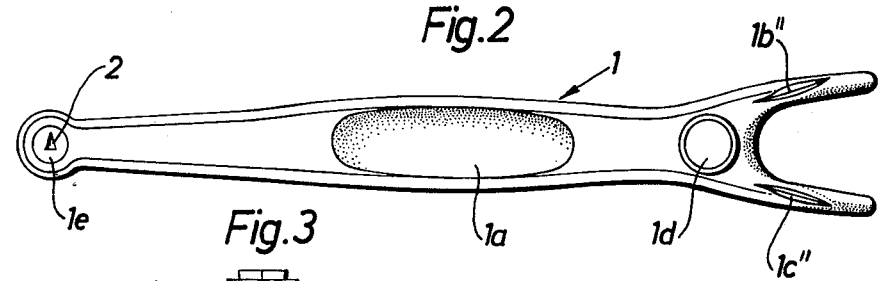
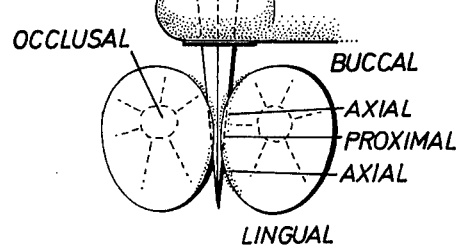
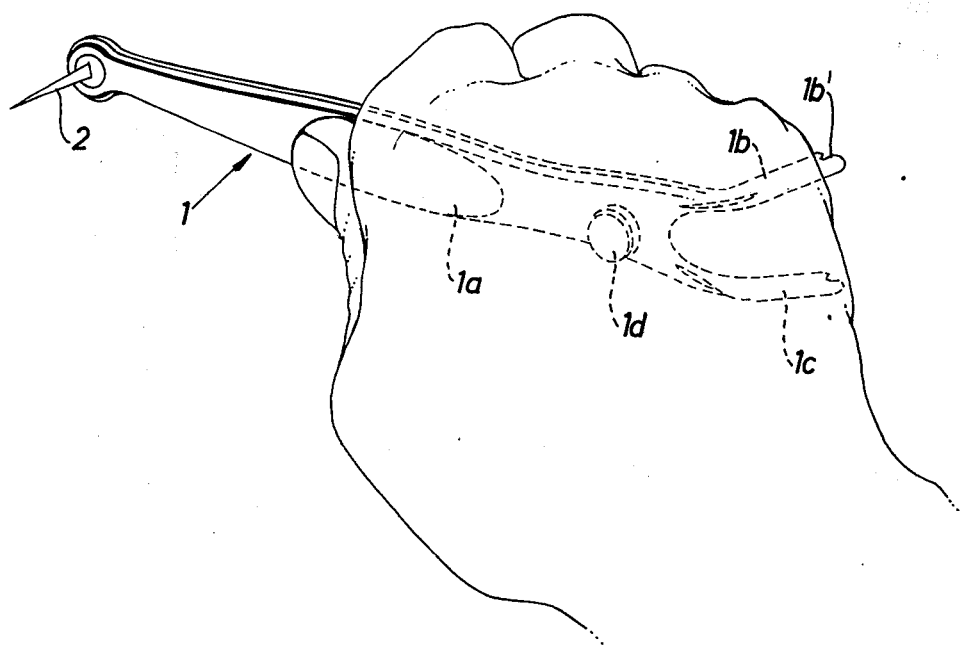

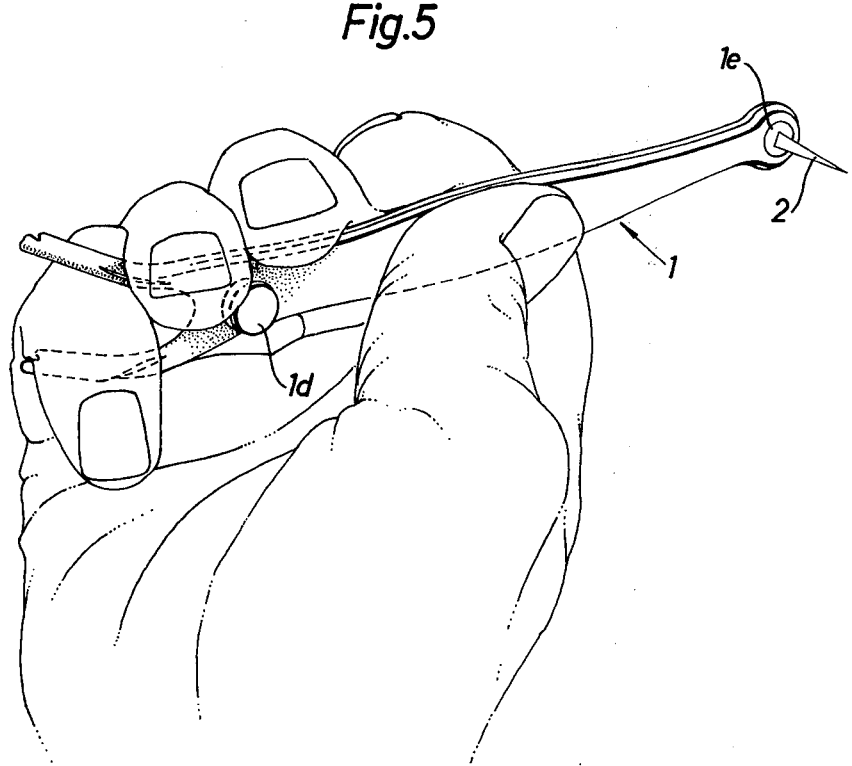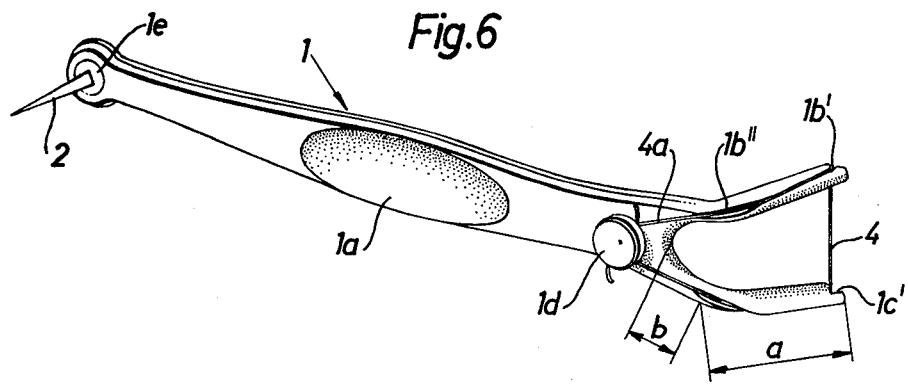

IMPLEMENT TO FACILITATE REMOVING BACTERIAL COATING FROM THE INTERSTITIAL AREAS OF ADJACENT TEETH AND CLEANING THE CREVICES THEREBETWEEN

The present invention relates to an implement to facilitate removing bacterial coating from the interstitial areas of adjacent teeth and cleaning the crevices therebetween.

An implement the primary object of which is to facilitate the removal of bacterial coating (plaque) from the interstitial areas of adjacent teeth and cleaning the crevices therebetween comprising a handle adapted to be held by the hand, at one end equipped with an applicator or a toothpick, preferably one being tapered and having a triangular cross section, which is frictionally held substantially at right angle to the plane of the handle in a bushing mounted in a hole in the handle at its end and adapted to swivel full circle to facilitate the entry of the pick into the area between adjacent teeth for the purpose of cleaning and massage.

A further object of the invention is to provide an implement the handle of which extends at its remote end into a bent-up portion to strengthen the grip of the hand on the handle. Another object of the invention is to provide an implement in which the bent-up portion has a fork-like shape and is adapted to support a dental floss stretched between the extreme ends of the tines of the fork for use in cleaning the interdental areas supplementary to the use of the toothpick.

The present invention relates to an implement for cleaning teeth, particularly a device of special usefulness in cleaning the axial and proximal surfaces of adjacent teeth for the removal of plaque (bacterial coating) thereon.

Recent advances in scientific research have shown more clearly than heretofore that the main etiological factor concerning the two dominating dental disorders, in fact from a practical standpoint the only ones, i.e. caries and periodontitis, resides in the accumulation of microorganisms (bacteria) which gather daily on the surfaces of the teeth that adjoin the gums, commencing at the neck of the teeth (the dental crevices).

If the accoumlation of bacteria were removed every day the dental disorders, of which they are the cause, might be prevented.

The commonly used toothbrush is, in a way, well adapted for use in cleaning the buccal and lingual surfaces, as well as the occlusal surfaces of the teeth but it should be noted that the cleaning utility of the toothbrush is limited to these areas only. Recent scientific investigations have proved that the axial and approximal surfaces are not satisfactorily cleaned by the use of a toothbrush.

For the latter purpose two different methods have been employed, namely,

A. The use of a straight toothpick of wood or plastic or metal with preferably a triangular cross section. The toothpick is pushed into the crevice between the teeth from the check-side of the mouth and is forced forward so hard that the sides of the toothpick are rubbed against the axial and proximal surfaces of two adjacent teeth.

B. The use of a dental floss which is stretched, and forced by hand, into the crevice between two adjacent teeth and is rubbed against the teeth.

The practical application of said methods has not been entirely successful, however. It has been, largely, a waste of time. Often the toothpick breaks; the dental floss is difficult to administer by hand and has a tendency to break.

The aforesaid disabilities have been particularly noticeable in connection with the cleaning of teeth surfaces in the vicinity of the axial angles. It has been found particularly difficult, almost impossible, to administer the toothpick in these quarters manually from the direction of the tongue. Also the manipulation of the floss requires a dexterity of high order, rarely found, to cause the floss to pass along the whole of the axial and approximal surfaces.

The task of developing an implement that provides the necessary tension in the dental floss and that rapidly engenders the manual skill in the operator which is a pre-requisite for the successful use of such an implement, has been found difficult in view of the fact that the use of the implement must, to be successful, lead to the removal, not only of scraps of food or the like, but particularly of the plaque.

A number of different instruments to facilitate cleaning the crevices between adjacent teeth are previously known. Such instruments generally comprise a holder having a fixed applicator at one end, or a holder in the shape of a fork or the like, between the tines of which a dental floss is stretched or a wax-covered tape ("Dentotape") is fastened.

According to the present invention the tooth cleaning implement comprises an applicator, preferably a toothpick of previously known design that tapers towards one end, which pick is frictionally held substantially perpendicularly to the plane of the handle in a traversing hole in a bushing mounted in a transversal boring at the end of the handle and adapted to swivel full circle.

It has been suggested heretofore, as pointed out, to mount a toothpick on a handle for use in tooth cleaning. For example, the U.S. Pat. No. 1,996,205 shows an instrument for treating teeth comprising a handle having at one end a tapering hole in which a toothpick having a tapering end is inserted and frictionally held in a fixed position with the assistance of cotton or the like that may be used to enclose the pick.

In contradistinction to the fixed toothpick implement thus previously disclosed the object of the present invention is to provide a dental instrument by the use of which the cleaning of the interdental areas, particularly the axial and proximal surfaces, is made possible thanks to a novel feature embodying a swiveling toothpick of triangular cross-section mounted on the handle referred to in the foregoing. Thereby, the pick readily enters into the crevices between two adjacent teeth without unnecessary, and possibly harmful, effort on the part of the user to force it into position.

Moreover, by having been adapted to swivel the triangular tapering pick or applicator readily adjusts itself to the shape of the interstitial areas of the teeth, to provide an efficient cleaning of the axial and proximal tooth surfaces and thus to remove the plaque.

In order to afford the user a steady grip of the instrument the remote end of the handle is preferably extended into a bent-up portion for engagement with the hand gripping the handle. Further, the bent-up portion may be conveniently shaped as a fork-like structure with two diverging tines, for engagement with one or more fingers of the handle-gripping hand, and at the same time to afford a means of providing a support for a dental floss that may be stretched, when desired, between the tines for use in supplementary cleaning of the pertinent tooth surfaces. For this latter purpose the tines may be provided with slightly helical tracks in the region of their upward bend so that the dental floss may be guided from a fastening means on the underside of the handle, along the tracks, and on the outside of the tines to notches provided at the extreme ends thereof. The dental floss may be stretched by hand and again secured at the fastening means, thereby biasing the tines together at the gap between their ends, to maintain adequate tension in the dental floss. To impart requisite strength and resilience to the tines the tracks may comprise longitudinal pits of slightly helical extension bordered by sides designed to contribute to the flexural strength of the tines without unnecessarily adding to their weight.

The improved dental instrument according to the invention is preferably made of plastic. Owing to the simplicity of its design the implement according to the invention is inexpensive to make. It is easy to use and has proved to be more efficient than similar implements heretofore known which concern the removal of plaque on the axial and proximal surfaces of adjacent teeth.

The preferred embodiment of the invention will be more clearly apparent by reference to the accompanying drawing, in which FIG. 1 is a side view of the handle with the mounting of the toothpick according to the invention shown in part section.

FIG. 2 is a bottom plan view of the implement according to the invention shown FIG. 1 with the bentup portion shaped like a fork.

FIG. 3 shows a plan view of two adjacent teeth at the collum region indicating the pertinent plaque-covered axial and proximal surfaces and the toothpick in position for cleaning.

FIG. 4 indicates, in a perspective view, the user's hand gripping the instrument with the outer edge of the hand engaging the fork.

FIG. 5 indicates the use's hand gripping the instrument with the fingers engaging the fork.

FIG. 6 is a perspective view of the implement according to the invention shown in FIG. 2, with the toothpick and the thread in position, ready for use.

In the drawing corresponding parts in the several figures are indicated by the same reference characters.

It will be seen from the drawing that the dental implement according to the invention comprises an elongated handle 1, having a substantially flat, approximately rectangular cross section with rounded corners. The handle 1 has sufficient size and appropriate shape to afford the user a steady grip of the instrument. For this purpose the underside of the handle is suitably provided with a recess 1a for cooperation with the thumb of the gripping hand to enable the user to hold the instrument firmly. Preferably the remote end B of the handle is extended into a bent-up portion for engagement with the outer edge of the hand and the fingers gripping the handle, as has been indicated in FIG. 4 and FIG. 5.

A toothpick or applictor 2 is mounted at the end A of the handle 1, substantially at right angle to the plane P thereof. For this purpose a transversal boring is provided at the end A of the handle which is at this point conveniently circular in shape. An axially rotatable bushing 1e is mounted in the boring, as is indicated in FIGS. 1–4. The bushing 1e is equipped with a central traversing hole 1e' adapted to receive and firmly hold by friction an applicator 2, for instance a toothpick, preferably of wood and of previously known design characterized by a triangular cross-section. The bushing 1e is adapted to swivel full circle around its own axis. By this means the toothpick 2 is automatically brought into correct position for entrance into the crevice between adjacent teeth, and an efficient cleaning operation is made possible on the pertinent surfaces of the teeth.

The position of the toothpick during cleaning is indicated in FIG. 3.

It is foreseen, according to the invention, that the bent-up portion of the handle may be given a fork-like shape having two diverging tines 1b and 1c provided with tracks 1b'' and 1c'' of slightly helical design and adapted to guide a dental floss 4, when such a floss is stretched from a fastening means 1d on the underside of the handle, over the outside of the tines to notches 1b', 1c' at the extreme ends of the tines and back to the fastening means 1d, the floss thereby being stretched across the gap between the notches 1b', 1c'.

The angle $\alpha$ of the plane P' of the bent-up portion to the plane P of the handle may lie within a sector of 5°–90°, preferably 60°–55°. The length of the tines may vary from 10–40 mm, preferably 22–28 mm; the length of the bent-up portion may vary from 20–26 mm and the length of the straight portion b from 7–2 mm.

The operation of the implement according to the invention will be evident from the foregoing description. The user firmly inserts the applicator, for example a tapering toothpick 2 of a commercially available type having a triangular cross section, in the hole 1e' in the bushing 1e. After very short practice he will be able effectively to employ the instrument in cleaning the interdental surfaces by rubbing and massaging, for the pick will by itself turn into the correct position by means of the revolving bushing. The user will, therefore, be able to hold the handle in the position that he finds the least strennous.

Supplementary to the use of the toothpick the cleaning may be carried out by means of the dental floss at the remote end B of the handle.

The user fastens one end of a piece of dental floss 4 at the fastening device 1d. A coil of the thread 4a is thereupon laid through one of the identical tracks 1b'' or 1c'', for example the track 1b'', passed by way of the notch 1b' across the gap between the tines 1b and 1c over to the notch 1c' and from there through the track 1c'' back to the fastening device 1d. The user pulls the dental floss sufficiently hard to bias the tines together so that the needed tension set up in the floss will be maintained when he secures the latter at the fastening device 1d. Surplus floss is conveniently cut off. It should be noted that the floss snugly adjoins the handle and the tines and there is only one passage of floss, namely that between the notches 1b' and 1c', free for use in the cleaning operation. In other words, in this example of the implement according to the invention there is no danger that the floss passing between the fastening device 1d and the notches 1b', 1c' becomes entangled during the cleaning operation: the part of the floss that is not engaged in the latter is secured firmly by the fastening device and is covered by the user's hand holding the implement. Moreover, any desired tension can be readily set up in the floss and adjusted by hand, and the user is not dependent on any mechanical contrivance to keep the floss under tension.

By adjusting the design of the bushing 1e in a manner known in the art the toothpick can be made to lean sideways under pressure in relation to the plane P without interference with the frictional fastening of the toothpick 2 in the hole 1e' in the boring, for example by mounting a spherical bushing as is known in the art. Thereby the cleaning of inaccessible interdental areas may be further facilitated.

It will be evident that the implement disclosed in the foregoing specification is particularly suited to cleaning the areas between adjacent teeth in that the user has at his disposal an instrument that is light, yet strong and flexible, easily held by the hand and adapted for use with facility in the most inaccessible dental regions of both the maxilla and the mandible. The novel design of the applicator assembly embodying a swivelling action enables the user effectively to clean the interdental areas and he may, if he chooses, supplement this action with the use of the dental floss at the other end of the handle.

The implement according to the invention is the result of extensive research and experimentation which has led to the development of a light, strong and practical instrument which is, moreover, inexpensive to manufacture.

In the foregoing disclosure only embodiments illustrating the invention have been set forth but it will be readily seen by anyone skilled in the art that many details of the implement may be changed within the scope of the invention.

What is claimed is:

1. A tooth cleaning instrument for manual use in removing bacterial coating (plaque) from the interstitial surfaces of adjacent teeth and in cleaning the crevices therebetween, comprising:
    an elongate handle with opposite ends arranged for supporting different interstitial cleaning devices, said handle being configured for firm holding by the whole hand of the user outside of the mouth and for easily swinging either end portion into the mouth and into adjacency with the teeth;
    a pair of springy tines extending from one said end of the handle, said tines having fixed end portions coplanar with said handle and extending divergently from the end of said handle, said tines being bent intermediate the ends thereof into a common plane angled from the plane of the handle by an angle of about 5° to 90°, said tines having free ends for support of a dental floss in tension therebetween;
    a fastening device on said handle adjacent said tines for holding opposite end portions of said dental floss;
    an elongate and triangular cross-section toothpick having woodlike tooth cleaning surfaces;
    means for supporting said toothpick for rotation and limited off-perpendicular movement with respect to said handle and locating a transverse hole at the other end of said handle, said toothpick being frictionally and removably engaged in said hole substantially at right angles to the plane of said handle; said handle being flat and platelike with a shallow, rounded thumb recess intermediate its ends, said thumb recess and fastening device being on one side of said handle and spaced longitudinally apart and said tines extending away from the opposite side of said handle, said means rotatably supporting said toothpick including an aperture in said other handle end and a bushing member rotatably mounted in said aperture, said bushing member having said pick hole extending therethrough so as to enable at least circumferential self-orientation of the triangular cross-section pick on contact thereof with teeth without need for reorientation of the handle, said divergent bent tines and said one handle end cooperatively forming a cradle of sufficient width for insertion of a finger of the user, said cradle and recess assisting reliable gripping of said handle by the hand of the user for cleaning guidance of said toothpick, said tines carrying substantially helically disposed tracks each defined by a pair of raised ridges separated by a floss groove, which tracks extend divergently along said one side of said tines to the bend zones thereof and terminate in the oppositely facing outboard edges of said tines short of the free ends of said tines, so as to direct floss from said fastening means to the free ends of tines and also reinforce each said tine in its own plane.

2. An implement for manual removal of bacterial coating (plaque) from the interstitial surfaces of adjacent teeth and for cleaning the crevices therebetween, comprising:
    an elongate, substantially flat handle adapted to be gripped by the hand of the user and having at one end thereof a transverse bore;
    a bushing rotatably mounted in said transverse bore and having a central transverse hole;
    a toothpick member of a noncircular cross-section adapted for insertion between teeth and having an end portion dimensioned for frictional securement in said transverse hole of said bushing, said toothpick projecting substantially at a right angle to the plane of said handle, said bushing being capable of full circle rotation in said bore, such that said toothpick automatically rotationally orients itself upon insertion between adjacent teeth without need for a corresponding rotation or pivoting of the handle;
    a bent-up portion at the remote end of the handle angled from the plane of the handle, the bent-up portion of the handle having a forklike shape with two tines adapted to support a dental floss stretched between the extreme ends of the tines and a fastening means to secure the floss in a stretched condition, said tines throughout their length diverging from each other as they extend from the remote end of said handle, said tines at their inboard positions being located for a short distance (b) in the plane of said handle and thereupon projecting by way of smooth upward bends into limited straight extensions (a) at an angle ($\alpha$) less than 90° and in excess of 5° from said handle plane, said tines having tracks extending slightly helically upward and outward along the outside of said bends to the exterior sides of said tines, the inboard ends of said tracks being aimed toward said fastening means and the outboard ends of said tracks being aimed toward notches at the extreme ends of the tines to conduct and hold said dental floss in a stretched condition between the tines.

3. An implement according to claim 2, in which the angle ($\alpha$) is within a sector of 60°–55°.

4. An implement according to claim 3, in which the dimension of ($a + b$) has a range of 10–40 mm, preferably 22–28 mm, and the dimension of $a$ has a range of 20–26 mm and the dimenson of $b$ has a range of 7–2 mm.

5. An implement according to claim 4, in which said tracks comprise longitudinal slots bordered by sides designed to contribute to the flexural strength of said tines in the region of the bends without adding to the weight thereof.

6. An implement according to claim 5, in which said tines are biased together by maintaining tension in said thread.

7. An implement according to claim 6, in which the handle is made of plastic in one piece and the toothpick is made of wood.